United States Patent
Giap et al.

(10) Patent No.: US 9,895,253 B2
(45) Date of Patent: Feb. 20, 2018

(54) BALLOON IMMOBILIZATION DEVICE FOR RADIATION TREATMENT

(71) Applicants: Huan Giap, Rancho Santa Fe, CA (US); Fantine Giap, Rancho Santa Fe, CA (US); Bosco Giap, Rancho Santa Fe, CA (US)

(72) Inventors: Huan Giap, Rancho Santa Fe, CA (US); Fantine Giap, Rancho Santa Fe, CA (US); Bosco Giap, Rancho Santa Fe, CA (US)

( * ) Notice: Subject to any disclaimer, the term of this patent is extended or adjusted under 35 U.S.C. 154(b) by 208 days.

(21) Appl. No.: 14/444,857

(22) Filed: Jul. 28, 2014

(65) Prior Publication Data
US 2016/0022467 A1    Jan. 28, 2016

(51) Int. Cl.
| | | |
|---|---|---|
| A61M 29/02 | (2006.01) | |
| A61F 5/37 | (2006.01) | |
| A61N 5/10 | (2006.01) | |
| A61B 17/42 | (2006.01) | |
| A61B 17/22 | (2006.01) | |

(52) U.S. Cl.
CPC ............ *A61F 5/37* (2013.01); *A61N 5/10* (2013.01); *A61B 2017/22069* (2013.01); *A61B 2017/4216* (2013.01); *A61N 2005/1097* (2013.01)

(58) Field of Classification Search
CPC ..... A61F 5/37; A61N 5/10; A61N 2005/1097; A61B 2017/22069; A61B 2017/4216
USPC .............. 600/424, 2, 6, 29; 606/1, 119, 121, 606/191–197
See application file for complete search history.

(56) References Cited

U.S. PATENT DOCUMENTS

| | | | |
|---|---|---|---|
| 8,080,031 B2 | 12/2011 | Isham | |
| 8,241,317 B2 | 8/2012 | Isham et al. | |
| 8,500,771 B2 * | 8/2013 | Isham | A61B 5/411 606/197 |
| 8,603,129 B2 | 12/2013 | Isham | |
| 2003/0014008 A1 * | 1/2003 | Jacques | A61M 25/0023 604/96.01 |
| 2008/0033525 A1 * | 2/2008 | Shaked | A61B 17/12022 623/1.11 |
| 2012/0078177 A1 | 3/2012 | Isharn | |
| 2013/0109906 A1 | 5/2013 | Valoir | |
| 2014/0336689 A1 * | 11/2014 | Elton | A61M 25/104 606/194 |

(Continued)

*Primary Examiner* — Sanjay Cattungal
(74) *Attorney, Agent, or Firm* — Gary L. Eastman, Esq.; Eastman & McCartney LLP

(57) ABSTRACT

The Balloon Immobilization Device for Radiation Treatment of the present invention includes a catheter assembly with radiopaque markers and one or more lumina. The catheter assembly consists of a flexible tube and inflatable balloon. The flexible tube has distal and proximal ends, with one or more separate lumina within and along the length of the flexible tube. At least one lumen is in fluid communication with the exterior of the flexible tube at the distal end and the interior of the inflatable balloon and at least one lumen in fluid communication with the exterior of the flexible tube at the distal end and the exterior of the flexible tube at the proximal end. The inflatable balloon varies in shape and size and is made of a radiopaque material having varying degrees of radiopacity. Radiopaque markers are located at different locations on the balloon and flexible tube.

15 Claims, 11 Drawing Sheets

(56) References Cited

U.S. PATENT DOCUMENTS

2015/0265816 A1* 9/2015 Campbell ........... A61M 25/104
606/194

* cited by examiner

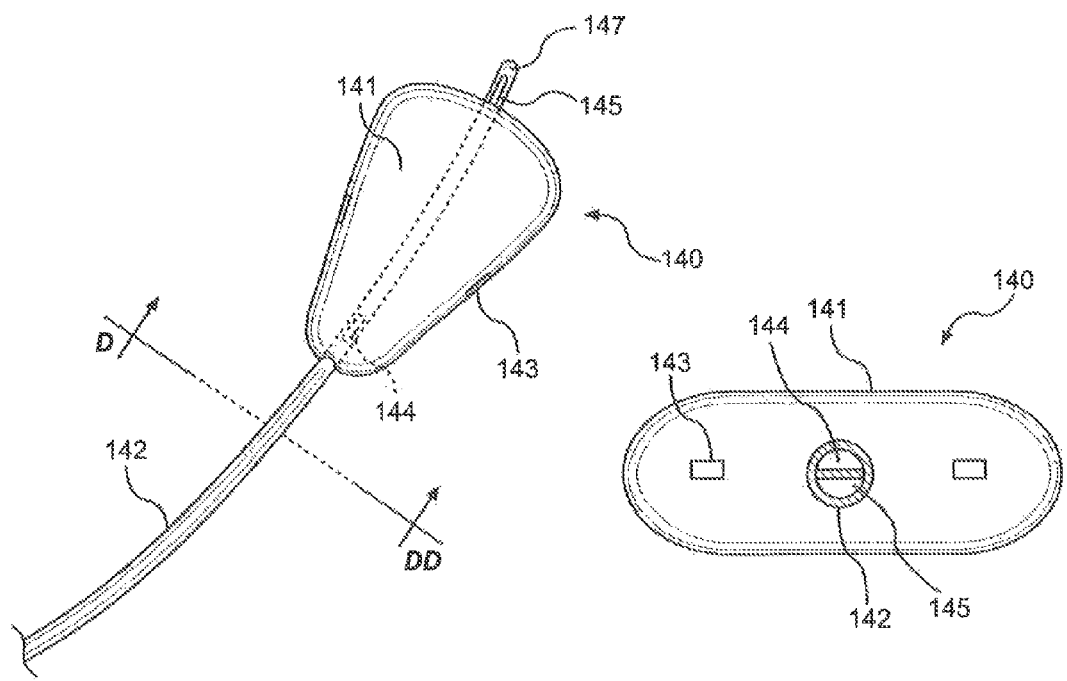
FIG. 19
FIG. 20
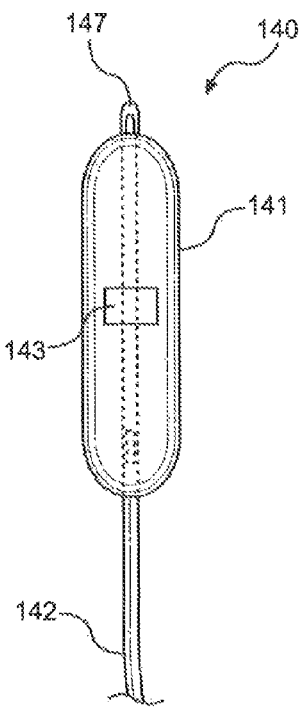
FIG. 21

BALLOON IMMOBILIZATION DEVICE FOR RADIATION TREATMENT

FIELD OF THE INVENTION

The present invention pertains generally to a device for use in the radiation treatment of cancers. More specifically, the present invention pertains to a device that can immobilize internal organs and provide spatial orientation information to healthcare providers during radiation therapy treatment for various cancers. The present invention is particularly, but not exclusively, useful as a device for the radiation therapy treatment of cancers of the bladder, vagina, rectum, and uterus.

BACKGROUND OF THE INVENTION

Radiation therapy is the medical use of high doses of ionizing radiation and typically used in the treatment of cancer to kill malignant cells. Radiation therapy can be used as a primary treatment or used in conjunction with other treatments, such as chemotherapy or surgery. In addition to cancerous cells, radiation therapy can damage healthy cells, making it imperative that treatment is carefully planned to minimize side effects. The type of radiation treatment given to cancer patients is dependent on many factors, including the type of cancer, stages of cancer, and the location of the cancer within the body.

Radiation therapy is used to treat many types of cancer, including: breast, bladder, vaginal, uterine, ovarian colon, rectal, kidney, lung, prostate, and thyroid cancers. Each type of cancer has specific treatment options. For example, in bladder cancer, radiation treatment typically involves the use of Intensity-Modulated Radiation Therapy (IMRT) that utilizes a computer-controlled linear accelerator. In IMRT, the beam from the linear accelerator is focused on a predetermined location based on a three-dimensional shape of the tumor acquired through computer tomography (CT) or magnetic resonance images (MRI). The three-dimensional image is made prior to beginning treatment. Small marks on the skin are made along the treatment area, pinpointing the telemetry of the beam so as not to damage healthy cells.

However, some tumors do not have a consistent, precise position because of the nature and location of the cancer in the internal organs. For example, radiation therapy for patients with bladder cancer is difficult due to the anatomy of the bladder. The bladder is an elastic organ, which frequently contracts and expands with urine. Organ motion and deformation (change in shape) prevent the accurate localization of the radiation beam to the tumor and as a result exposes normal healthy organs to unnecessary radiation. Therefore, the three-dimensional image acquired prior to starting a radiation therapy plan may not be useful for subsequent radiation appointments if, in comparison to when the image was produced, the bladder has expanded or deflated with urine. Consequently, if the beam is not in the precise position, it could cause damage to healthy cells.

There are approximately 75,000 new cases of bladder cancer per year in the United States. In the majority of cases, surgery is used to treat patients with bladder cancer by surgically removing all or part of the bladder (cystectomy). This is especially true for patients with muscle invasive transitional-cell carcinoma of the bladder, where the cancer invades the muscular layer of the bladder wall. As a replacement for the full or partial removal of the bladder, the bladder is reconstructed from portions of the bowel. This is a major surgery with significant impact of a patients' quality of life due to incontinence. Alternatively, radiation and chemotherapy are used together to treat bladder cancer to avoid this particular surgery, called bladder-preservation therapy. Bladder preservation is essential to the quality of life of patients, and there has been an effort among the medical community to preserve the bladder in patients being treated for bladder cancer.

Clinical studies show that bladder patients undergoing chemo-radiation therapy have about a 50% survival rate (similar to surgery); however, about 20-30% of these patients surviving the chemo-radiation treatment have significant radiation damage to their bladder making it useless (incontinence). This serious side effect is due to the unnecessary exposure of the normal bladder to high doses of radiation during radiation treatment as a result of the change in shape and size of the bladder during the radiation treatment. The exposure to radiation typically last about 30 minutes per day, 5 days per week, for about 7 weeks. Due to the inaccurate delivery of radiation during bladder cancer treatment and its negative side effects, the radiation dosage delivered to the bladder tumor cannot be given as high as needed. The typical current dose of radiation to bladder tumors is about 6,300 to 6,500 rads (a "rad" is a unit of radiation treatment dosage), instead of the needed dose in the range of 7,000-8,000 rads for solid tumors. Any advancement in the precision of radiation treatment would increase the chances of having a safe and effective alternative to cystectomy.

One development towards addressing organ movement and its relation to radiation treatment has been the use of Image-Guided Radiation Therapy (IGRT). IGRT uses radiograph images in conjunction with a linear accelerator to improve the accuracy of daily targeting of the tumor. In IGRT the linear accelerator uses image technology (X-ray, CT scan) to take frequent images immediately prior to, and sometimes during treatment. This technology has been used in many cancers including bladder cancer. Although the use of this technology would improve chances of bladder preservation, it is still difficult to immobilize the bladder during the radiation treatment to limit organ movement and deformation. Moreover, it is also difficult to place markers within the bladder as a guide for radiation treatment without the use of invasive surgery.

There are currently devices that affect the shape of the bladder by continually draining urine. A Foley catheter may be used to continually drain urine from the body using a balloon and multiple lumina. One lumen drains urine from the bladder and another lumen fills the balloon with sterile water in order to prevent the balloon from slipping out of the bladder. However, the Foley catheter is primarily used for irrigation of the bladder and it is not designed to maintain the bladder in a constant shape and volume. The Foley catheter balloon is much smaller than the interior of the bladder and thus cannot control the expansion or contraction of the bladder. In addition, a Foley catheter is typically used as a more permanent solution to incontinence.

In light of the above, it would be advantageous to provide a means of reducing the exposure of healthy cells to harmful radiation. It would be further advantageous to provide an apparatus to immobilize the bladder or other elastic organ to retain its shape during radiation treatment to prevent damage to healthy cells and to minimize side effects. It would be further advantageous to provide an apparatus having stationary markers able to be removably inserted into the bladder or other elastic organ to guide any radiation treatment to the correct area of the tumor without the need for invasive surgery. By knowing the exact position of the tumor and surrounding critical organs, one can improve the treatment outcomes by increasing the dose of radiation to the tumor (hence, higher cure rate) and reducing the dose of radiation to the surrounding critical organs (less side effects and complications). Having this immobilization device will enhance the therapeutic windows of the treatment, i.e., increasing the cure rate and reducing the side effects of the treatment.

SUMMARY OF THE INVENTION

The Balloon Immobilization Device for Radiation Treatment of the present invention includes a catheter assembly with radiopaque markers and one or more lumina. The catheter assembly consists of a flexible tube and inflatable balloon. The flexible tube has distal and proximal ends, with one or more separate lumina within and along the length of the flexible tube. Radiopaque markers can be different shapes, sizes, and occupy different locations within the balloon and catheter depending on the use. In addition, the inflatable balloon is made of a radiopaque material having varying degrees of radiopacity, depending on the device's purpose and location.

In the preferred embodiment for use in bladder cancer treatment, the flexible tube distally trifurcates into three (3) distinct branches with separate lumina. Distance measurement markers (in centimeter or inches) are incorporated along the exterior of the flexible tube. Each of the three (3) lumina separates and occupies the inner space of each of the three (3) branches of the flexible tube. The first lumen is open on both ends to drain urine from the bladder into a drainage bag. The second lumen opens into the inflatable balloon and is used to introduce fluid or air to inflate the balloon. The third lumen is open on both ends and is used for irrigation or introducing medications or liquid radio-protector agents into the bladder. This third lumen can also be used as a channel to introduce a small thin electronic device to measure the actual radiation being delivered (in-vivo dosimeter).

The inflatable balloon is coupled to the flexible tube at the proximal end. The shape of the balloon can be elliptical, pyramidal, cylindrical, or spherical, and the size or volume can be small, medium, or large, depending on the volume of the bladder and organs. As stated previously, the inflatable balloon can have varying degrees of radiopacity, depending on its purpose and location. For example, depending on the location of the cancerous cells within the bladder and the orientation of the linear accelerator beam, it may be beneficial to shield specific areas from unnecessary radiation exposure that can be harmful to healthy cells by making parts of the balloon more or less radiopaque than others.

Within the inflatable balloon are one or more radiopaque markers to provide spatial orientation or other uses during radiation therapy. As previously mentioned, these radiopaque markers can be different shapes, sizes, and occupy different locations within the balloon depending on the use. For example, when the balloon is inflated within the bladder, one radiopaque marker may be located at the top of the balloon, and the another radiopaque marker may be located at the bottom of the balloon to orient the position of the bladder.

When in use, the inflatable balloon is positioned within the bladder and the proximal end of the flexible tube passes through the urethra. The distal end of the flexible tube remains outside the body and each lumen attaches to various devices depending on the purpose of each lumen. The first lumen continuously drains urine, so it can be connected to a urine drainage bag or other various fluid collecting apparatus. The second lumen is used to introduce fluid via a syringe or other device to inflate the balloon with a certain amount of fluid and then the lumen is locked via a 2-way stop valve. The third lumen is used to irrigate or introduce medications or radio-protector agents into the bladder. The inflatable balloon is inflated within the bladder to hold the bladder at a consistent volume and shape, as well as orient the markers within the bladder.

This embodiment can also be used in radiation therapy treatment for prostate cancer, the most common form of cancer in men. The prostate is a small, walnut-sized gland located directly below the bladder. The rectum is positioned posterior to both the prostate and the bladder. Given the close proximity of the prostate, bladder, and rectum, the change in bladder and rectum volume has a direct impact on the position of the prostate. Although it has been determined that rectal movement has a more significant effect on the position of the prostate, in certain situations it may be important to immobilize the bladder for radiation treatment of the prostate.

Another embodiment of the present invention can be used for limiting the movement of the rectum during radiation treatment of rectal cancer. Rectal cancer occurs when there is cancerous or abnormal cell growth in the lining of the rectum. Like the bladder, the rectal walls expand and contract as the organ fills and empties with fecal matter from the digestive process. Also like the bladder, the movement can make precise radiation therapy difficult. There are circumstances where only part of the rectal circumference is needed to be irradiated while sparing the uninvolved rectal areas from the radiation treatment portal. The movement and deformation of the rectum makes the precise delivery of radiation to these particular areas even more difficult.

In this embodiment, the inflatable balloon of the present invention would be oblong to fit the shape of the rectum and the size would vary depending on the volume of the rectum of the patient. One or more lumen would be used for the inflation of the inflatable balloon and for possible irrigation or introducing radio protector agents into the rectum. In addition, the configuration of radiopaque markers in the inflatable balloon could be used for multiple reasons, including information on the location of the cancerous cells in the lining of the rectum. In addition, the inflatable balloon can have varying degrees of radiopacity depending on the purpose of the device and can therefore shield untreated areas from any radiation.

As stated before, the rectum is positioned relatively close to the prostate and it is well established that the movement of the rectum has an impact on the position of the prostate. Therefore, this embodiment of the present invention could also be used to immobilize the rectum for more precise radiation therapy treatment for prostate cancer.

Although vaginal cancer is not common, this alternative embodiment of the Balloon Immobilization Device for Radiation Treatment of the present invention may be useful for the treatment of vaginal cancer. Vaginal cancer is a disease in which malignant cells form in the vagina, and radiation therapy is preferentially used in treatment of this cancer. In this embodiment, the inflatable balloon is positioned in the vagina with the flexible tube extending out of the body. The vagina is an elongated canal that extends from the outer female genitalia to the cervix. The inflatable balloon would be elongated in shape, but the size would vary subject to the individual patient's anatomy.

Depending on the purpose and circumstances of the case, one or more lumina could be used. The first lumen will inflate the inflatable balloon and another may be used for possible irrigation or introducing radio protector agents into the vagina. The radiopaque markers can be used to aid in finding the location of the cancerous cells, without the use of invasive surgery to implant markers. In addition, the varying radiopacity of the inflatable balloon can shield healthy areas of the vagina from harmful radiation, while still exposing the area needing treatment.

In an alternative embodiment, the Balloon Immobilization Device for Radiation Treatment of the present invention could be used to maintain the shape of the corpus of the uterus during radiation treatment of uterine cancer. Uterine cancer occurs when there is a growth of abnormal cells in the lining of the uterus. Despite surgery as the main treatment for uterine cancer, radiation therapy is used and preferred over surgery as the main treatment for patients who are not a candidate for surgery, specifically the elderly and patients with significant morbidities. In this embodiment, the device will be inserted through the vagina and cervix, into the uterus. The inflatable balloon itself is positioned in the corpus of the uterus with the flexible tube extending out of the body. When a female is not pregnant, the uterus is flatter antero-posteriorly and is pyriform in shape. The inflatable balloon would be pyriform in shape, but the volume may vary subject to the individual patient's anatomy.

Depending on the purpose and circumstances of the case, one or more lumina could be used. The first lumen will inflate the inflatable balloon and another lumen may be used for possible irrigation or introducing radio protector agents into the uterus. Radiopaque markers can be used to aid healthcare professionals in locating the position of the cancerous cells, without the use of invasive surgery to implant markers. In addition, the varying radiopacity of the inflatable balloon can shield healthy areas of the uterus from harmful radiation, while still exposing the area or areas needing treatment.

BRIEF DESCRIPTION OF THE DRAWING

The nature, objects, and advantages of the present invention will become more apparent to those skilled in the art after considering the following detailed description in connection with the accompanying drawings, in which like reference numerals designate like parts throughout, and wherein:

FIG. 19 is a plan view of an alternative embodiment of the Balloon Immobilization Device for Radiation Treatment of the present invention showing a pyriform-shaped inflated inflatable balloon with radiopaque markers;

FIG. 20 is a cross-sectional view of the flexible tube taken along line D-DD of FIG. 19 showing the distal end of the inflatable balloon and radiopaque markers;

FIG. 21 is a side view of an alternative embodiment of the Balloon Immobilization Device for Radiation Treatment of the present invention of FIG. 19 showing an inflated inflatable balloon with a radiopaque marker;

DETAILED DESCRIPTION OF A PREFERRED EMBODIMENT

Figure 1:
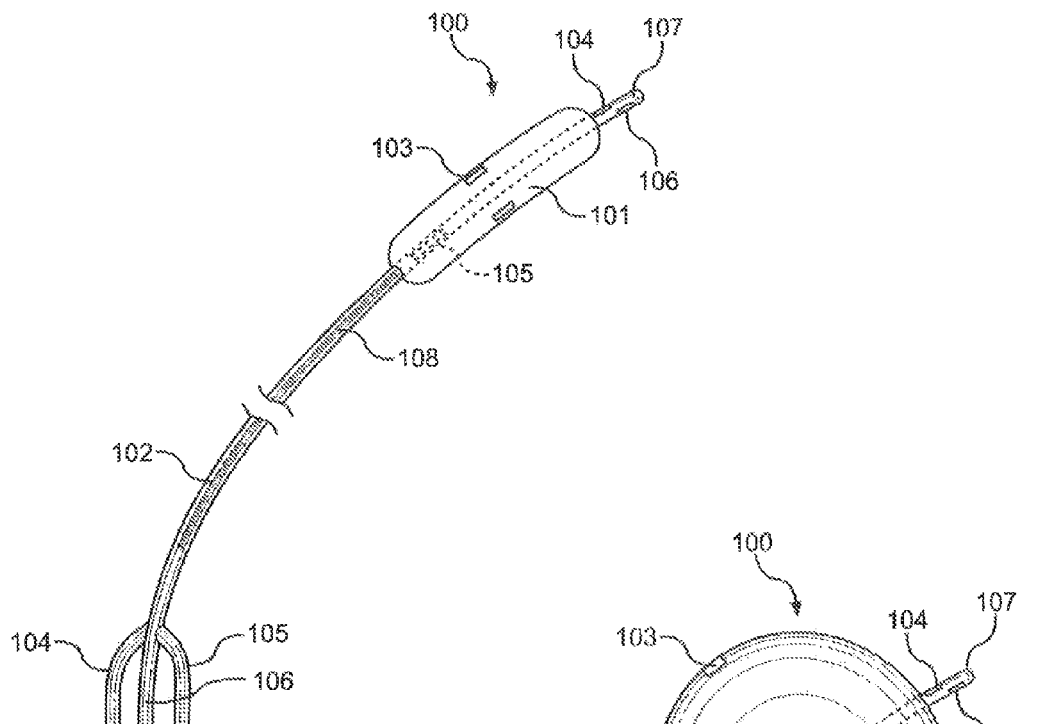
FIG. 1 is a plan view of the Balloon Immobilization Device for Radiation Treatment of the present invention, showing an elliptical deflated inflatable balloon, radiopaque markers, and a flexible tube having three (3) lumina distally trifurcating into three (3) separate branch tubes having a lumen corresponding to one of the three (3) lumina of the flexible tube.

Referring initially to FIG. 1, the preferred embodiment of the Balloon Immobilization Device for Radiation Treatment for bladder cancer of the present invention is shown and generally designated 100. The Balloon Immobilization Device for Radiation Treatment 100 consists of a flexible tube 102, a catheter tip 107, an inflatable balloon 101, and two radiopaque markers 103. The inflatable balloon 101 is made of an expandable membrane incorporated with slightly radiopaque materials. As shown, the inflatable balloon 101, when deflated, is oblong and thin enough to allow insertion into the urethra (not shown) or other orifices subsequently discussed.

The flexible tube 102 can be of any length depending on the use of the Balloon Immobilization Device for Radiation Treatment 100 of the present invention. Within the flexible tube 102 are three (3) separate lumina, first lumen 104, second lumen 105, and third lumen 106. The flexible tube 102 distally trifurcates into three (3) distinct branches and each of the three (3) lumina, first lumen 104, second lumen 105, and third lumen 106, occupies the inner space of each of the three (3) branches of the flexible tube 102.

The first lumen 104 begins at a first opening located within one of the trifurcated branches of the flexible tube 102 and extends through the flexible tube 102, through the inflatable balloon 101, and ends at a second opening at the catheter tip 107. Urine from the bladder (not shown) enters through the second opening of the first lumen 104 located in the catheter tip 107 and flows out through the first opening of the first lumen 104 located in the corresponding trifurcated branch tube.

The second lumen 105 begins at a first opening located within one of the trifurcated branches of the flexible tube 102, extends through the flexible tube 102, and ends at a second opening located on the flexible tube 102 within the inflatable balloon 101. The second lumen 105 is used to inflate said inflatable balloon 101 by injecting sterile fluid through the first opening of the second lumen 105 which then enters the balloon at the second opening located within the inflatable balloon 101.

The third lumen 106 begins at a first opening located within one of the trifurcated branches of the flexible tube 102 and extends through the flexible tube 102, through the inflatable balloon 101, and ends at a second opening at the catheter tip 107. The third lumen 106 is used for irrigation or introducing radio protector agents into the bladder. Additional lumina can be added depending on the use of the Balloon Immobilization Device for Radiation Treatment 100 of the present invention.

By having multiple lumina exposed to the interior cavity of the bladder, the simultaneous introduction and removal of fluids can be achieved. The third lumen 106 can be used to introduce a fluid while the first lumen 104 can remove any unwanted fluid from within the bladder. This enables the Balloon Immobilization Device for Radiation Treatment 100 of to flush a bladder of radio protector agents after treatment has been completed for the session. Further, the multiple lumina can be used to introduce multiple different fluids separately into the bladder.

On the outer surface of the flexible tube 102, distance measurement markers 108 are incorporated. The distance measurement markers 108 are physical graduations which designates a unit of measurement such as inches or centimeters. In conjunction with the physical graduations, alphanumeric characters are used. The distance measurement markers 108 aid in determining how far the Balloon Immobilization Device for Radiation Treatment 100 is inserted within a patient.

Figure 2:
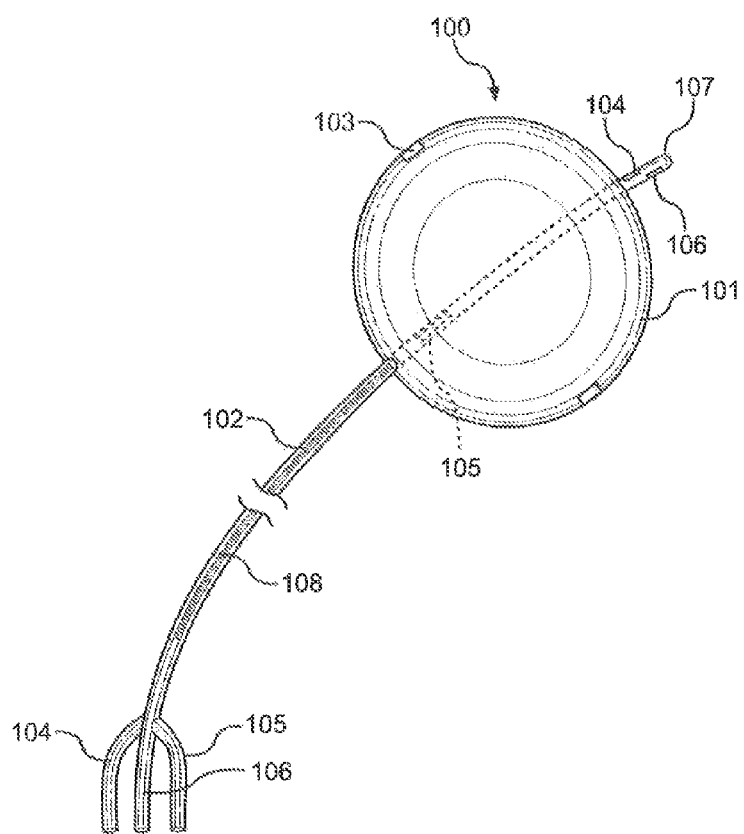
FIG. 2 is a plan view of the Balloon Immobilization Device for Radiation Treatment of the present invention, showing an elliptical inflated inflatable balloon, radiopaque markers, and a flexible tube having three (3) lumina distally trifurcating into three (3) separate branch tubes having a lumen corresponding to one of the three (3) lumina of the flexible tube.

When the inflatable balloon 101 is inflated, as shown in FIG. 2, the inflatable balloon 101 is elliptical in shape with radiopaque markers 103 located in the mid-section of the inflatable balloon 101. In FIG. 2, the radiopaque markers 103 are rectangular. However, the radiopaque markers 103 can be different shapes, sizes, and occupy different locations within the inflatable balloon 101 depending on the use of the Balloon Immobilization Device for Radiation Treatment 100 of the present invention.

Based on the material of the radiopaque markers 103, the radiopaque markers 103 may have varying degrees of radiopacity. Radiopacity refers to the relative inability of electromagnetic radiation to pass through a particular material. This is particularly beneficial when using electromagnetic radiation imaging devices to determine the location of a tumor. While easily passing through non-radiopaque portions of the Balloon Immobilization Device for Radiation Treatment 100 and the patient, the radiopaque markers 103 will inhibit the passing of electromagnetic radiation of the imaging device, thereby enabling the imaging device to determine the precise location of the radiopaque markers 103. The radiopaque markers 103 can then be used as a reference point to locate the tumor. The material used for the radiopaque markers may vary depending on the level of radiopacity desired and can include titanium, tungsten, barium sulfate, zirconium oxide or other various radiopaque materials.

Figure 3:
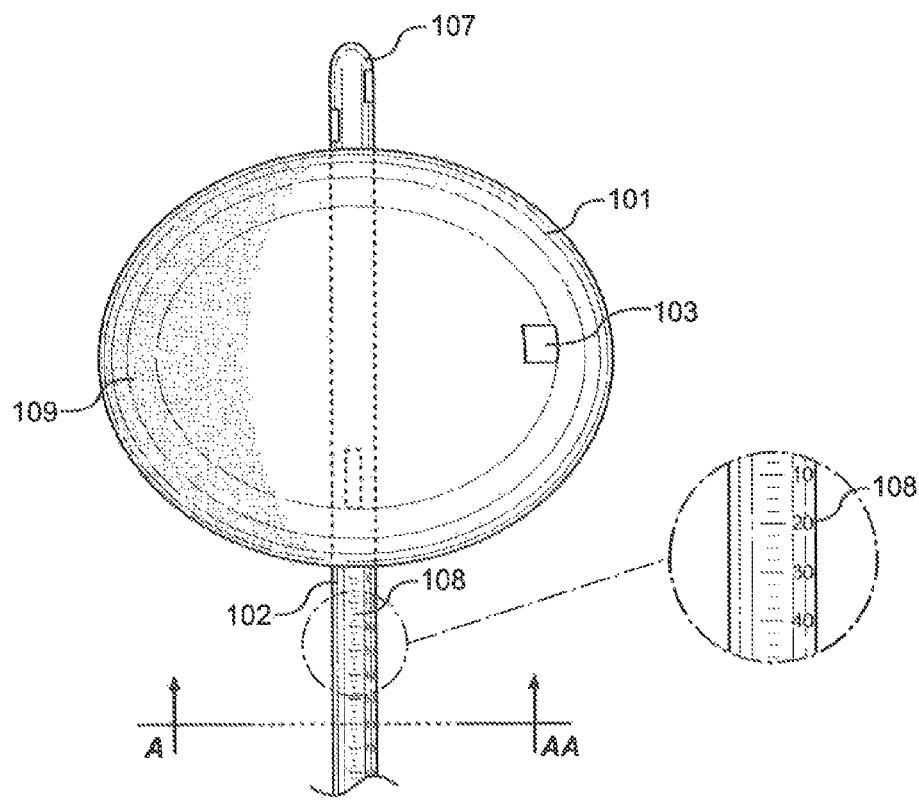
FIG. 3 is a plan view of the Balloon Immobilization Device for Radiation Treatment of the present invention, showing an inflated inflatable balloon with a radiopaque marker and an area of high radiopacity.

In addition to radiopaque markers 103, the Balloon Immobilization Device for Radiation Treatment 100 of the present invention can also have varying degrees of radiopacity. In FIG. 3, a plan view of a variation of the preferred embodiment of the Balloon Immobilization Device for Radiation Treatment 100 of the present invention is shown. The inflatable balloon 101 is inflated, with a radiopaque marker 103 located on the midsection of the inflatable balloon 101. Additionally, there is an area of high radiopacity 109 incorporated in the inflatable balloon 101 shown as an area with surface shading. When in use, the areas of high radiopacity 109 can shield healthy cells from potential exposure to harmful radiation. As shown, the area of high radiopacity 101 covers approximately 30% of the surface area of the inflatable balloon. However, it is contemplated that the area of high radiopacity 109 may cover anywhere between 1% and 100% of the surface area of the inflatable balloon 101 and may have various patterns and shapes. This allows the areas of high radiopacity 109 to be adapted to various circumstances and situations to shield the healthy cells from the harmful radiation experienced during treatments.

Figure 4:
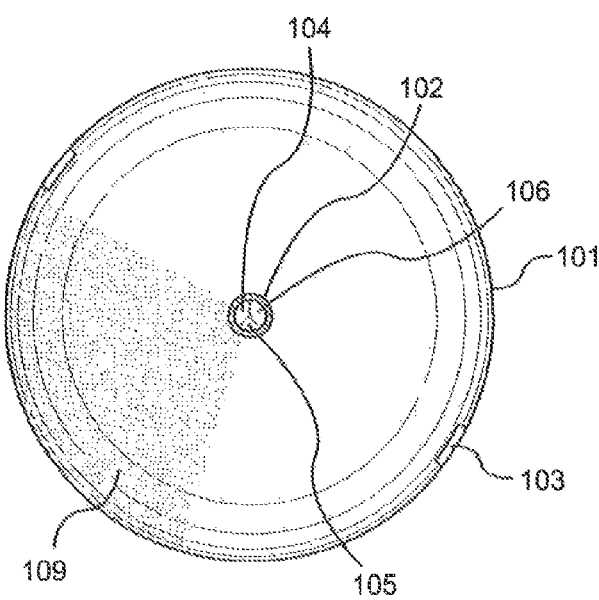
FIG. 4 is a cross-section view of the flexible tube having three (3) lumina taken along the line A-AA of FIG. 3 showing the distal end of the inflated inflatable balloon, an area of high radiopacity, and two (2) radiopaque markers.

The radiopacity of the radiopaque markers 103 is higher than that of the area of high radiopacity 109 to allow the imaging device to differentiate between the two and precisely locate the radiopaque markers 103. As clearly shown in FIG. 3, the distance measurement markers 108 are graduations with alpha-numeric characters designating each graduation. FIG. 4 is the cross-sectional view of the flexible tube 102 containing first lumen 104, second lumen 105, and third lumen 106 taken along the line A-AA of FIG. 3, showing the distal end of the inflated inflatable balloon 101, a radiopaque marker 103, and an area of high radiopacity 109.

Figure 5:
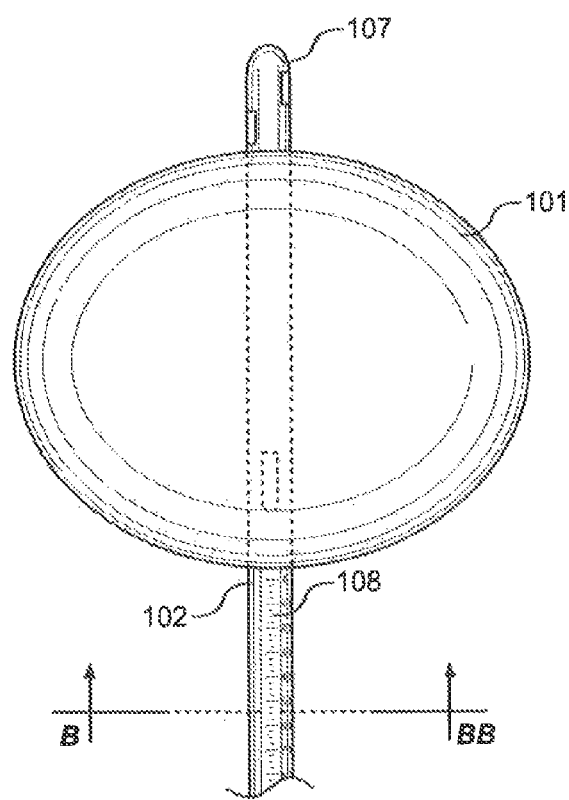
FIG. 5 is a plan view of the Balloon Immobilization Device for Radiation Treatment of the present invention showing the inflatable balloon and flexible tube with no area of high radiopacity or radiopaque markers.
Figure 6:
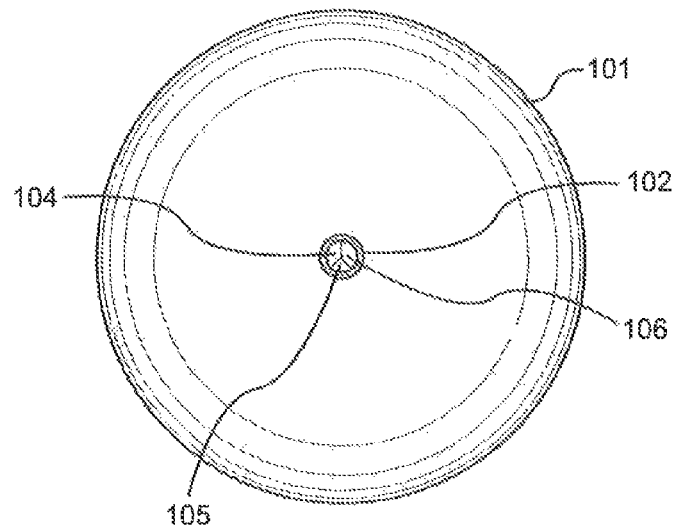
FIG. 6 is a cross-sectional view of the flexible tube containing three (3) lumina taken along line B-BB of FIG. 5 showing the distal end of the inflated inflatable balloon with no radiopaque markers.

In contrast, FIG. 5 is a plan view of the Balloon Immobilization Device for Radiation Treatment 100 of the present invention showing the inflatable balloon 101 with no area of high radiopacity or radiopaque markers and flexible tube 102. FIG. 6 is a cross-sectional view of the flexible tube 102 containing first lumen 104, second lumen 105, and third lumen 106 taken along line B-BB of FIG. 5 showing the distal end of the inflated inflatable balloon with no radiopaque markers or areas of high radiopacity.

Figure 7:
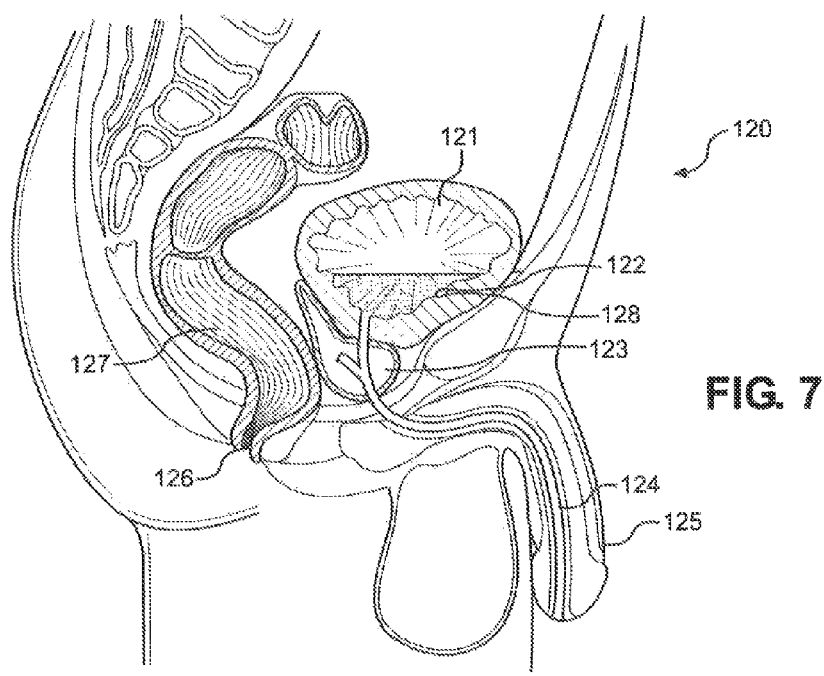
FIG. 7 is a cross-sectional view of the male anatomy showing a partially filled bladder having a tumor at position one on the inner wall of the bladder.
Figure 8:
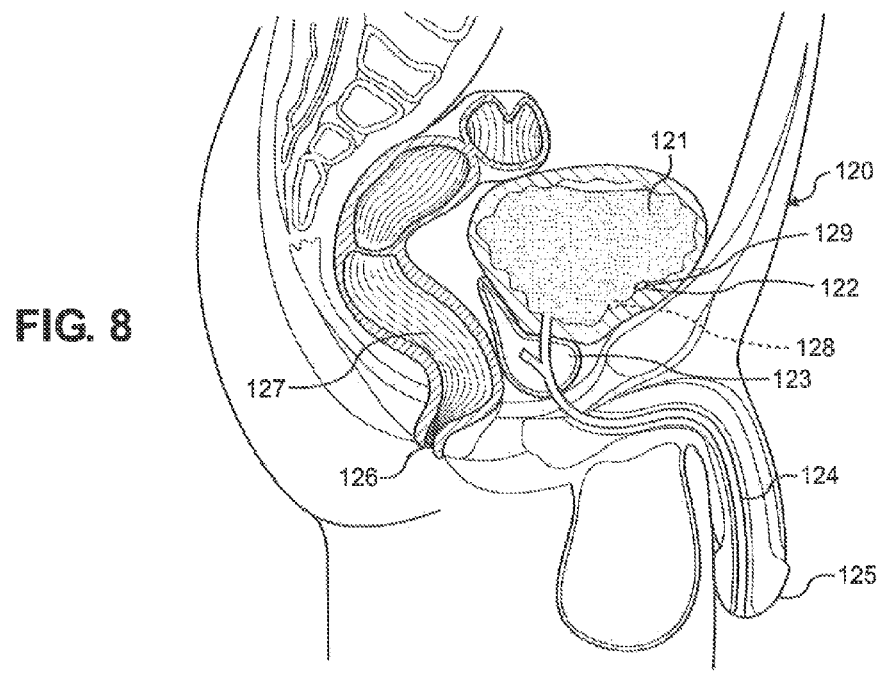
FIG. 8 is a cross-sectional view of the male anatomy showing a full bladder having a tumor at position two on the wall of the bladder.

In FIG. 7, the cross-section of the male anatomy 120 is shown. The bladder 121 is located just above the prostate 123 and is shown partially filled with urine. In this state, the bladder 121 is slightly collapsed in upon itself. A tumor 122 is located on the inner wall of the bladder 121. In this state, the tumor 122 on the wall of the bladder 121 is at position one 128. However, as the bladder continues to receive urine from the kidneys (not shown) the spatial position of the tumor 122 will continue to shift. In FIG. 8, the cross-section of the male anatomy is shown. Here, the bladder 121 is full, and therefore the tumor 122 position has shifted to position two 129.

Figure 9:
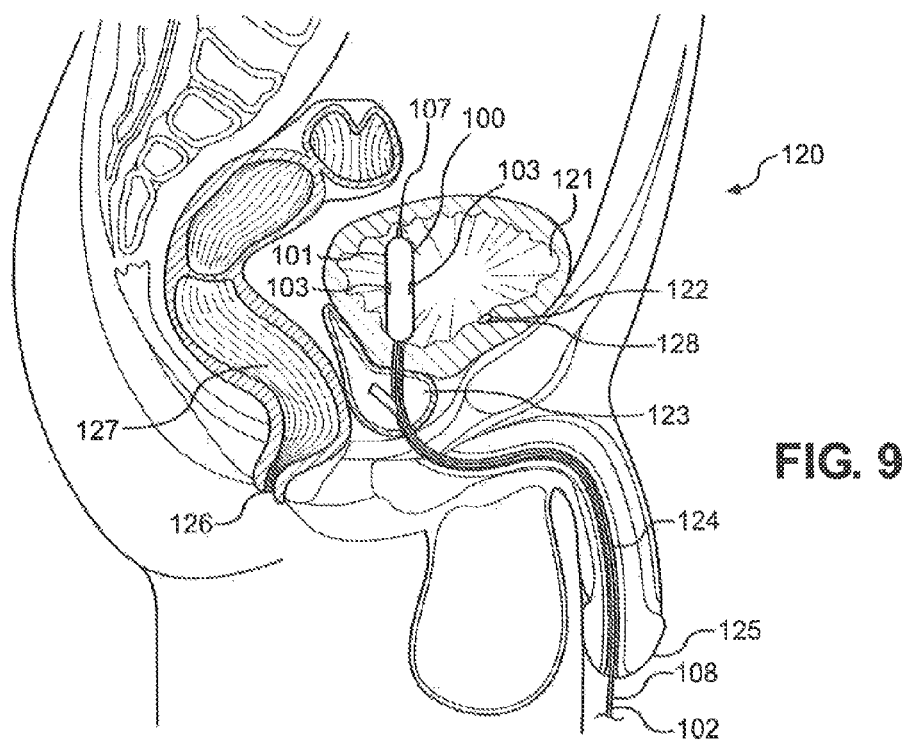
FIG. 9 is a cross-sectional view of the male anatomy showing a deflated Balloon Immobilization Device for Radiation Treatment of the present invention inserted within the bladder with the flexible tube extending out of the bladder through the urethra and penis.

In FIG. 9, the cross-section of the male anatomy is shown 120 with the deflated Balloon Immobilization Device for Radiation Treatment 100 of the present invention inserted into the bladder 121. When inserted, the proximal end of the Balloon Immobilization Device for Radiation Treatment 100 of the present invention is inserted into the urethra 124 through the penis 125. The deflated inflatable balloon 101 remains in the bladder 121, while the flexible tube 102 extends from the bladder 121, through the urethra 124 and out of the penis 125, where it distally trifurcates into three (3) branches (not shown), each branch containing one of the three (3) separate lumen (not shown). The distance measurement markers 108 indicate how far the balloon 101 has been inserted.

Figure 10:
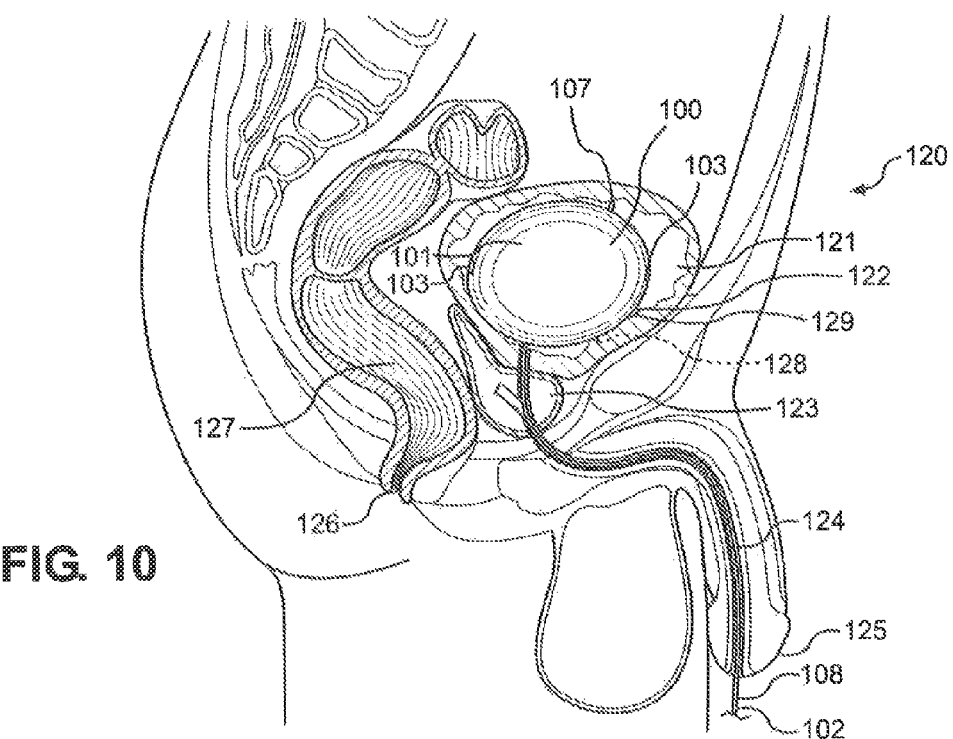
FIG. 10 is the cross-sectional view of the male anatomy showing an inflated Balloon Immobilization Device for Radiation Treatment of the present invention inserted within the bladder, with the flexible tube extending out of the bladder, through the urethra and out of the penis.

In FIG. 10, the inflatable balloon 101 of the Balloon Immobilization Device for Radiation Treatment 100 of the present invention has been inflated by the second lumen 105 (not shown). The first lumen 104 (not shown) drains urine from the bladder 121 through the opening on the catheter tip 107 located at the top of the inflatable balloon 101. In addition, the third lumen 106 (not shown) can provide irrigation, or introduce radio protectant agents into the bladder 121.

In its inflated state, the Balloon Immobilization Device for Radiation Treatment 100 of the present invention fixes the bladder 121 at a constant shape and volume thereby fixing the tumor 122 at location two 129. Additionally, the inflation of the inflatable balloon 101 positions the radiopaque markers 103 at a constant spatial location within the bladder 121. The radiopaque markers 103 provide a reference point in which all other points of various objects may be based upon, such as the relative location of the bladder 121 and the tumor 122. Due to the constant shape and volume of the inflatable balloon 101, the radiopaque markers 103 provide a reliable, constant, and precise reference point. As a result, the radiopaque markers 103 are used to guide health care providers to the precise position of the tumor 122 on the inner wall of the bladder 121.

The distal end of the flexible tube 102 remains outside the body and each lumen attaches to various devices depending on the purpose of each lumen. The first lumen 104 (not shown) continuously drains urine, so it can be connected to a urine drainage bag or other fluid collecting apparatus. The second lumen 105 (not shown) is used to introduce fluid via a syringe or other device to inflate the balloon and then locked via a 2-way stop valve or other mechanism. The third lumen 106 (not shown) is used to irrigate or introduce medications or radio-protector agents into the bladder 121. A valve or other apparatus may be used to close the third lumen 106 until it is utilized to introduce medication or agents into the bladder.

Figures 11, 12:
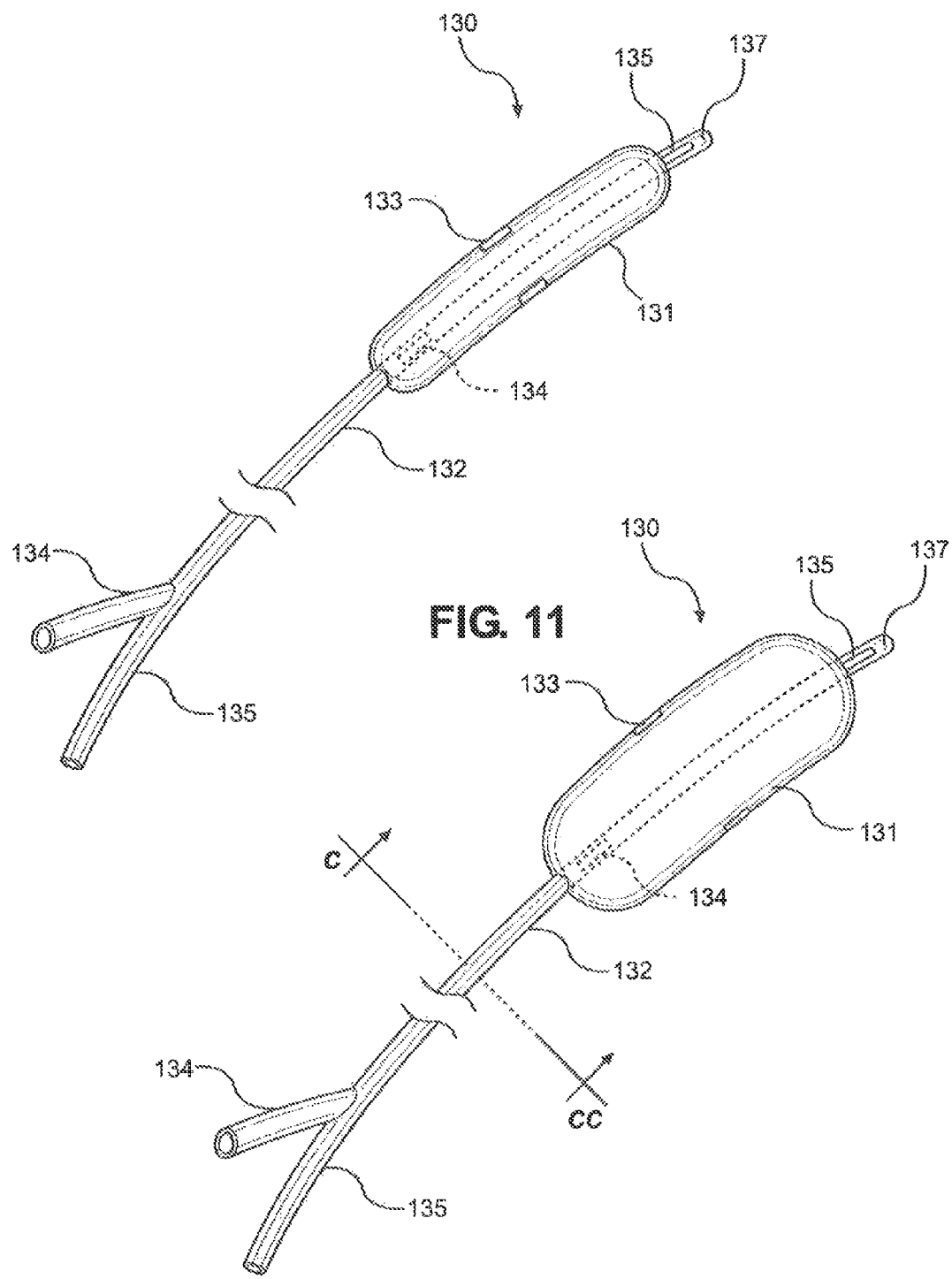
FIG. 11 is a plan view of an alternative embodiment of the Balloon Immobilization Device for Radiation Treatment of the present invention showing an elongated, deflated inflatable balloon with radiopaque markers, and a flexible tube having two (2) lumina bifurcating into two (2) branch tubes having a lumen corresponding to one (1) of the two (2) flexible tube lumina.
FIG. 12 is a plan view of an alternative embodiment of the Balloon Immobilization Device for Radiation Treatment of the present invention showing an elongated inflated inflatable balloon with radiopaque markers, and a flexible tube having two (2) lumina bifurcating into two (2) branch tubes having a lumen corresponding to one (1) of the two (2) flexible tube lumina.

Now referring to FIG. 11, a plan view of an alternative embodiment of the Balloon Immobilization Device for Radiation Treatment of the present invention is shown and generally designated 130. This embodiment of the immobilization device 130 also includes a catheter assembly consisting of a flexible tube 132, a catheter tip 137, and an inflatable balloon 131. The inflatable balloon 131 is made of a slightly radiopaque material. Similarly to the Balloon Immobilization Device for Radiation Treatment 100 shown in FIGS. 3 and 4, the inflatable balloon 131 of the current embodiment of the immobilization device 130 of the present invention can also have varying degrees of radiopacity, depending on the use of the device. As shown in FIG. 11, the inflatable balloon 131, when deflated, is oblong and thin enough to allow insertion into the anus (not shown) or other orifices subsequently discussed. In addition, depending on the use of the immobilization device 130 of the present invention, the length of the inflatable balloon 131 will vary.

Continuing with FIG. 11, two radiopaque markers 133 are shown located on the midsection of the inflatable balloon 131 and positioned at 180 degrees of each other and are rectangular in shape. However, the radiopaque markers 133 can be different shapes, sizes, and occupy different locations on the balloon depending on the use of the device. The flexible tube 132 is shown and can be of varying lengths. Within the flexible tube 132 are two (2) lumina, first lumen 134 and second lumen 135. The flexible tube 132 distally bifurcates into two (2) distinct branches and each of the two (2) lumina, first lumen 134 and second lumen 135, occupies the inner space of each of the two (2) branches of the flexible tube 132.

The first lumen 134 begins at a first opening located within one of the bifurcated branches of the flexible tube 132 and extends through the flexible tube 132, through the inflatable balloon 131, and ends at a second opening located on the flexible tube 132 within the inflatable balloon 131. The first lumen 134 is used for inflating the inflatable balloon 131 by injecting sterile fluid through the first opening of the first lumen 134 which then enters the balloon at the second opening located within the inflatable balloon 131.

The second lumen 135 begins at a first opening located within one of the bifurcated branches of the flexible tube 132 and extends through the flexible tube 132, through the inflatable balloon 131, and ends at a second opening at the catheter tip 137. The second lumen 135 can be used for irrigation or for introducing radio protector agents into the area using an opening on catheter tip 137. Additional lumina could be added to flexible tube 132 depending on the uses of the Balloon Immobilization Device for Radiation Treatment 130 of the present invention. As shown, the flexible tube 132 does not have distance measurement markers. However, it is contemplated that distance measurement markets may be included without departing from the scope and spirit of the present invention.

In FIG. 12, the inflatable balloon 131 of the Balloon Immobilization Device for Radiation Treatment 130 of the present invention has been inflated by the first lumen 134. In its inflated state, the Balloon Immobilization Device for Radiation Treatment 130 of the present invention fixes the rectum (not shown) or other appropriate organ at a constant shape and volume.

Figure 13:
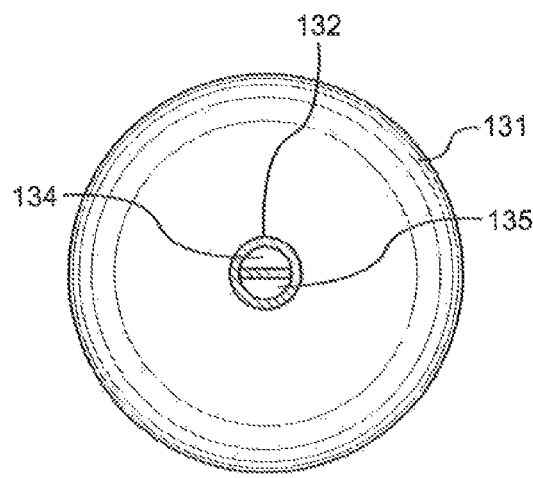
FIG. 13 is a cross-sectional view of the flexible tube taken along line C-CC of FIG. 12 showing the distal end of the inflated inflatable tube.

In FIG. 13, the cross-section of the Balloon Immobilization Device for Radiation Treatment 130 of the present invention taken along line C-CC of FIG. 12 is shown. The first and second lumen, 134 and 135 respectively, are visible within the flexible tube 132. The bottom or distal view of the oblong-shaped inflatable balloon 131 is also shown.

Figure 14:
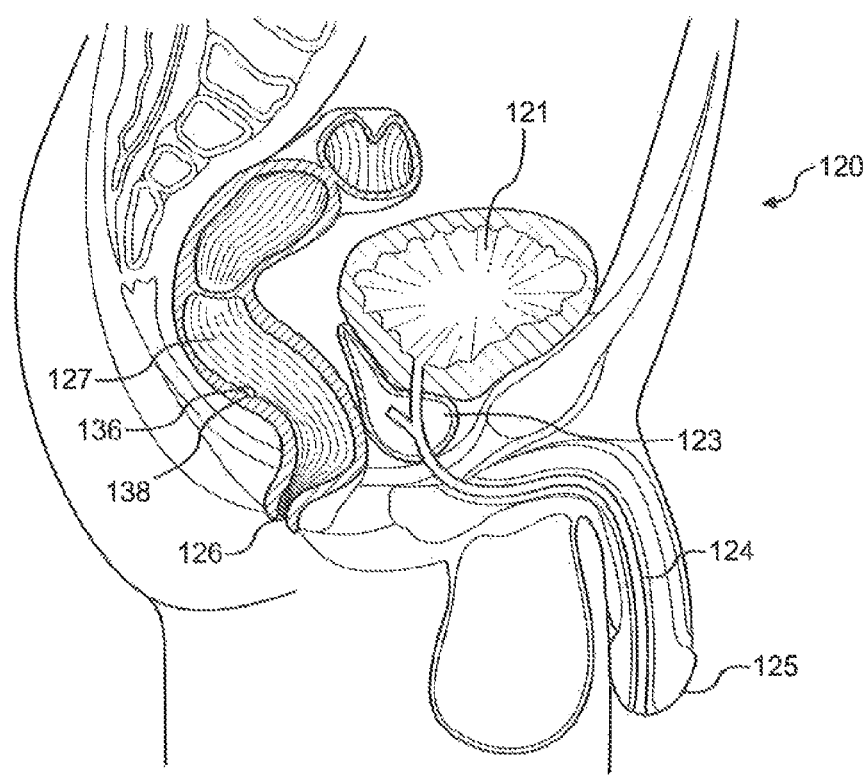
FIG. 14 is a cross-sectional view of the male anatomy showing a tumor on the surface of the inner wall of the rectum.

Referring now to FIG. 14, a cross-section of the male anatomy 120 is shown. The rectum 127 sits posteriorly to the bladder 121 and prostate 123. Like the bladder 121, the rectum 127 expands and contracts as the organ fills and empties with fecal matter from the digestive process. A tumor 136 is located at position one 138 on the rectal 127 wall. However as with the tumor 122 located on the bladder 121 in FIGS. 1 and 8, the tumor 136 on the wall of the rectum 127 can also have different spatial positioning depending on the expanding and contracting nature of the rectum 127.

Figure 15:
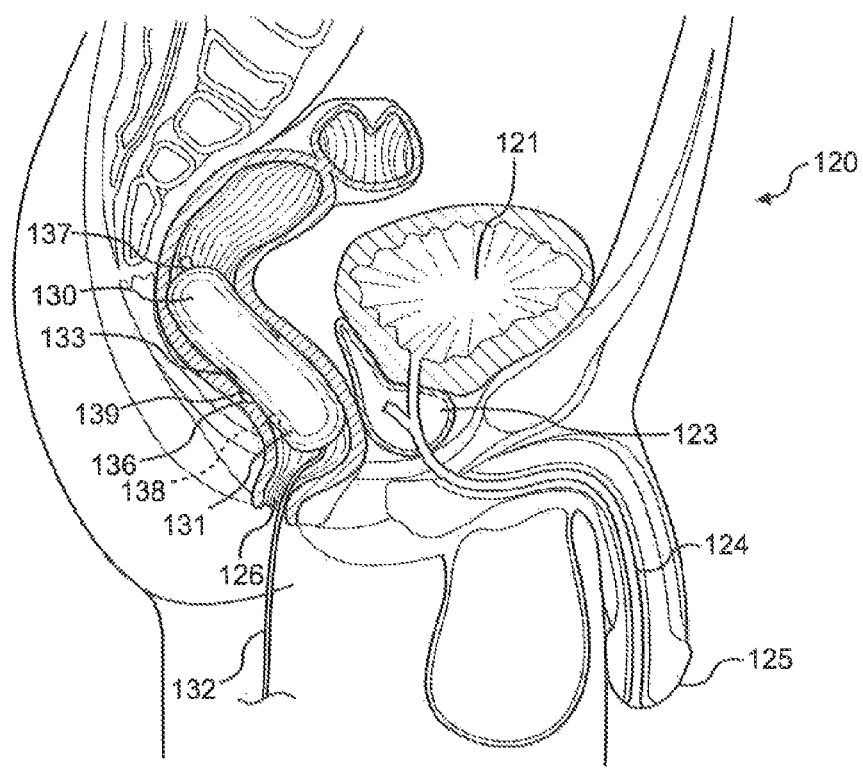
FIG. 15 is a cross-sectional view of the male anatomy showing an inflated alternative embodiment of the Balloon Immobilization Device for Radiation Treatment of the present invention within the rectum with the flexible tube extending out of the rectum and through the anus.

In FIG. 15, a cross-section of the male anatomy 120 is shown with the Balloon Immobilization Device for Radiation Treatment 130 of the present invention inserted and inflated within the rectum 127. The immobilization device 130 of the present invention is inserted, uninflated (as shown in FIG. 11), into the rectum 127 through the anus 126. When inserted, the inflatable oblong-shaped inflatable balloon 131 is then inflated by the first lumen 134 (not shown). The flexible tube 132 extends out of the rectum 127 and anus 126.

When the inflatable balloon 131 is inflated, the inflatable balloon 131 presses against the walls of the rectum 127 and fixes the rectum 127 at a constant shape and volume. The expansion of the inflatable balloon 131 against the rectum 127 expands the rectum thereby moving tumor 136 from position one 138 to position two 139. In addition, the radiopaque markers 133 serves as reference points and are used to guide health care providers to the precise position of the tumor 136 located on the inner wall of the rectum 127.

Figure 16:
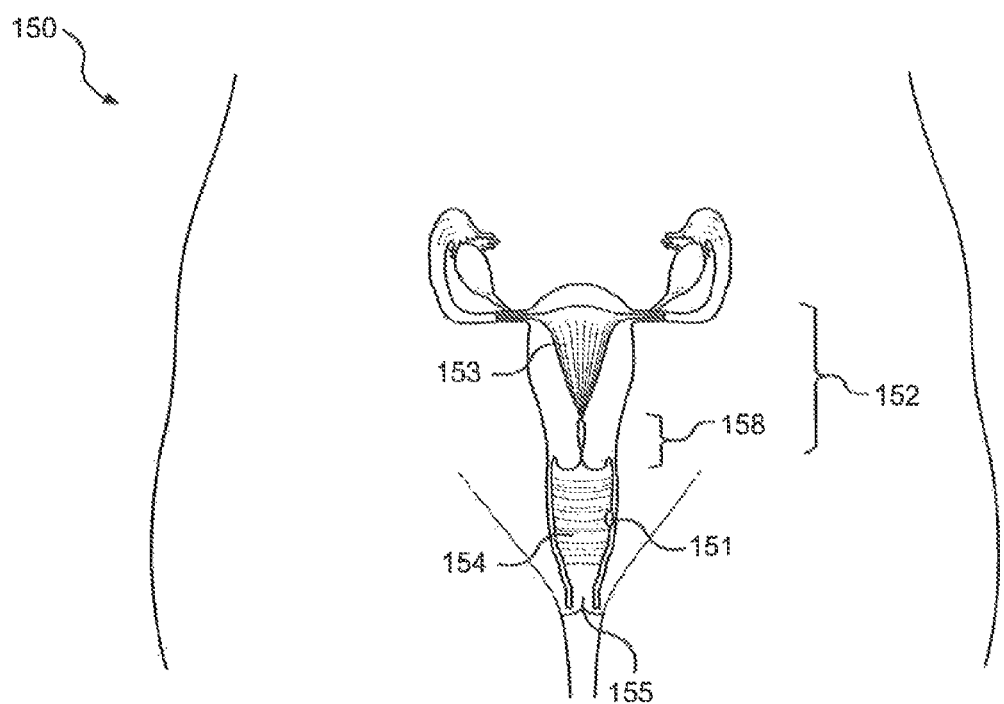
FIG. 16 is an internal antero-posterior cross-sectional view of the female reproductive organs showing a tumor on the internal wall of the vagina.
Figure 17:
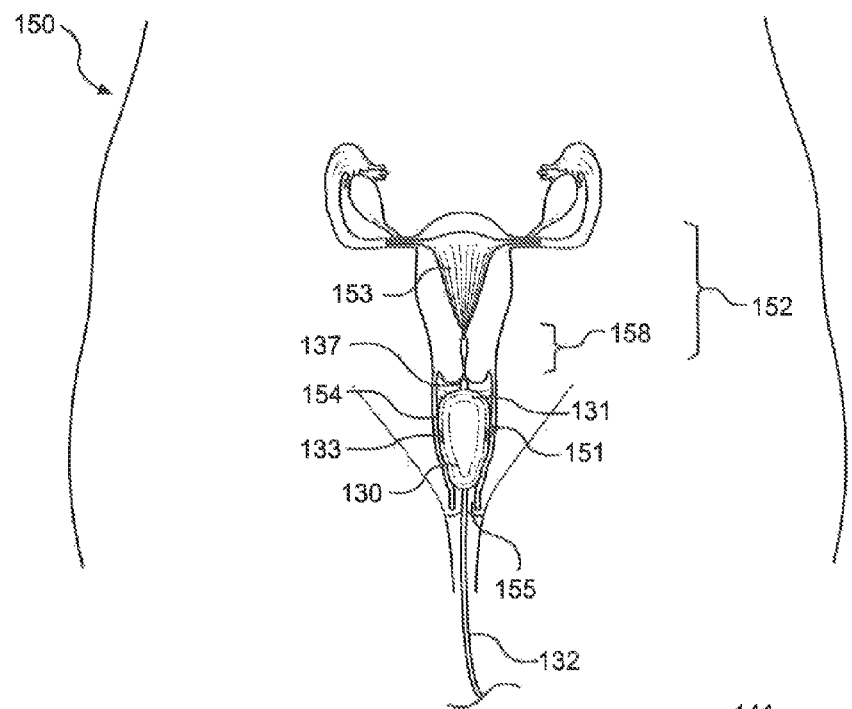
FIG. 17 is an internal antero-posterior cross-sectional view of the female reproductive anatomy showing the inflated elongated inflatable balloon within the vagina, with the flexible tube extending out of the vagina.

The alternative embodiment of the Balloon Immobilization Device for Radiation Treatment 130 of the present invention can also be used in the vaginal canal 154 shown in FIGS. 16 and 17. Referring first to FIG. 16, the internal cross-sectional anterior view of the female reproductive system 150 is shown. The vagina 154 is a canal that connects to the cervix 158, the lower part of the uterus 152. A tumor 151 is shown on the inner wall of the vagina 154.

Now referring to FIG. 17, an internal cross-sectional, anterior view of the female reproductive system 150 is shown with the alternative embodiment of the Balloon Immobilization Device for Radiation Treatment 130 of the present invention inserted and inflated within the vaginal canal 154. The Balloon Immobilization Device for Radiation Treatment 130 of the present invention is inserted, uninflated (as shown in FIG. 11), into the vaginal canal 154 with flexible tube 132 extending out of the vaginal canal 154 and vaginal opening 155. When inserted, the inflatable oblong-shaped inflatable balloon 131 is then inflated by the first lumen 134 (not shown) and presses against the walls of the vaginal canal 154. When the inflatable balloon 131 is inflated, the vaginal canal 154 is fixed at a constant shape and volume and tumor 151 is fixed at a particular position as a result. In addition, radiopaque markers 133 are used to guide health care providers to the precise position of the tumor 151 located on the inner wall of the vaginal canal 154.

Figure 18:
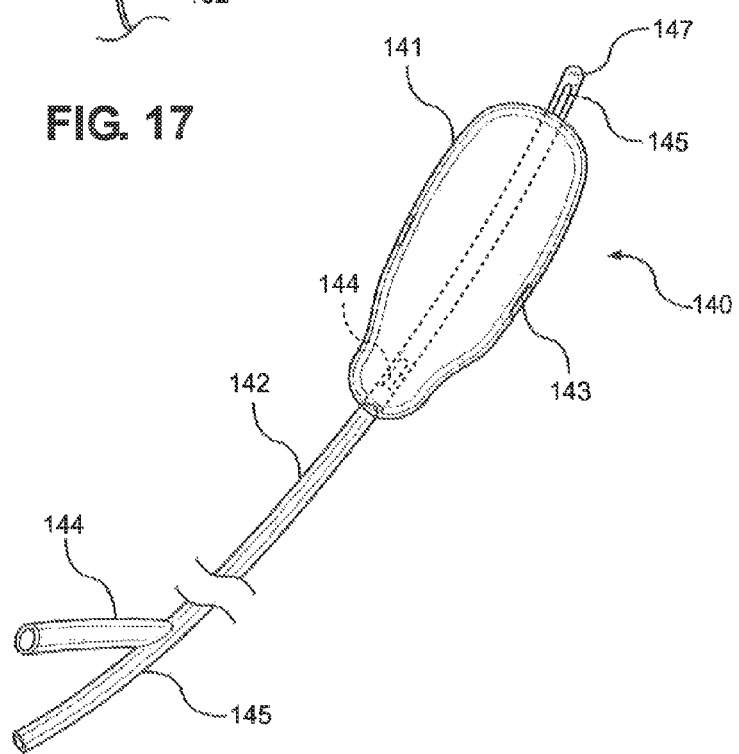
FIG. 18 is a plan view of an alternative embodiment of the Balloon Immobilization Device for Radiation Treatment of the present invention showing a deflated inflatable balloon with radiopaque markers and a flexible tube.

In FIG. 18, a plan view of an alternative embodiment of the Balloon Immobilization Device for Radiation Treatment of the present invention is shown and is generally designated 140. This embodiment of the Balloon Immobilization Device for Radiation Treatment 140 of the present invention also includes a catheter assembly consisting of a flexible tube 142, a catheter tip 147 and inflatable balloon 141. The inflatable balloon 141 is made of a slightly radiopaque material. However, as shown in FIGS. 3 and 4 for the Balloon Immobilization Device for Radiation Treatment 100 of the present invention for use with bladder cancer, the inflatable balloon 141 of the current embodiment of the Balloon Immobilization Device for Radiation Treatment 130 of the present invention can also have varying degrees of radiopacity, depending on the use of the device.

The inflatable balloon 141, when deflated, is oblong, but with more material located at the top of the inflatable balloon 141. In addition, the deflated inflatable balloon 141 must be thin enough to allow insertion into the vaginal canal 154, through the cervix 158, and into the corpus of the uterus 153 (not shown). However, a cervical clamp (not shown) could be used to expand the cervix 158. In addition, the length of the inflatable balloon 141 of the Balloon Immobilization Device for Radiation Treatment 140 of the present invention will vary depending on the uterus 152.

Two radiopaque markers 143 are shown located on the midsection of the inflatable balloon 141 and positioned at 180 degrees of each other and are rectangular in shape. However, the radiopaque markers can be different shapes, sizes, and occupy different locations on the inflatable balloon 141 depending on the use of the device. The flexible tube 142 is shown and can be varying lengths. Within the flexible tube 142 are two (2) lumina, first lumen 144 and second lumen 145.

The first lumen 144 begins at a first opening located within one of the bifurcated branches of the flexible tube 142 and extends through the flexible tube 142, through the inflatable balloon 141, and ends at a second opening located on the flexible tube 142 within the inflatable balloon 141. The first lumen 144 is used for inflating the inflatable balloon 141 by injecting sterile fluid through the first opening of the first lumen 144 which then enters the balloon at the second opening located within the inflatable balloon 141.

The second lumen 145 begins at a first opening located within one of the bifurcated branches of the flexible tube 142 and extends through the flexible tube 142, through the inflatable balloon 141, and ends at a second opening at the catheter tip 147. The second lumen 145 can be used for irrigation or for introducing radio protector agents into the area using an opening on catheter tip 147. Additional lumina could be added to flexible tube 142 depending on the uses of the Balloon Immobilization Device for Radiation Treatment 140 of the present invention. Additional lumina could be added depending on the uses of the immobilization device. As shown, the flexible tube 142 does not have distance measurement markers. However, it is contemplated that distance measurement markets may be included without departing from the scope and spirit of the present invention.

In FIG. 19, the inflatable balloon 141 of the Balloon Immobilization Device for Radiation Treatment 140 of the present invention has been inflated by the first lumen 144 (not shown). In its inflated state, the Balloon Immobilization Device for Radiation Treatment 140 of the present invention is pyriform-shaped, but flattened antero-posteriorly. When inflated, the Balloon Immobilization Device for Radiation Treatment 140 of the present invention fixes the uterus 152 (not shown) at a constant shape and volume.

In FIG. 20, the cross-section of the flexible tube 142 of the immobilization device 140 of the present invention taken along line D-DD of FIG. 19 is shown. The first lumen 144 and second lumen 145 are visible within the flexible tube 142. The bottom or distal view of the pyriform-shaped inflatable balloon 142 is shown and the radiopaque markers 143 can be seen.

FIG. 21 is the side view of the Balloon Immobilization Device for Radiation Treatment 140 of the present invention. Although pyriform-shaped, the device is flattened antero-posteriorly, giving the side view of the Balloon Immobilization Device for Radiation Treatment 140 an oblong shape.

Figure 22:
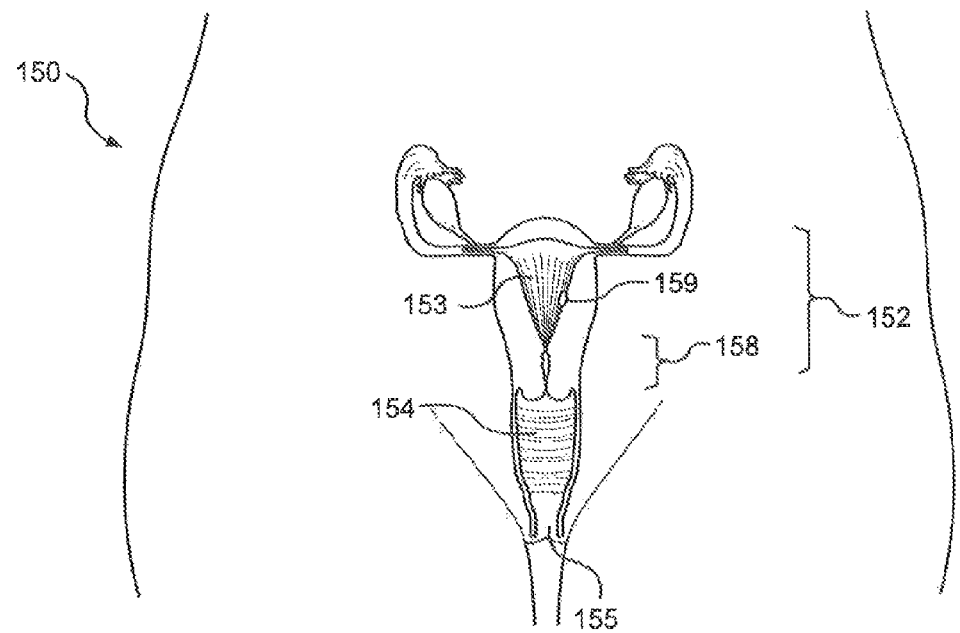
FIG. 22 is an internal antero-posterior cross-sectional view of the female reproductive anatomy showing a tumor on the internal walls of the uterus.

Referring to FIG. 22, the internal cross-sectional anterior view of the female reproductive system 150 is shown. The vagina 154 is a canal that connects to the cervix 158, the lower part of the uterus 152. The uterus 152 is a hollow, pyriform-shaped organ that is divided into two parts: the cervix 158 and the corpus 153 of the uterus 152. A tumor 159 is shown on the inner wall of the corpus 153 of the uterus 152.

Figure 23:
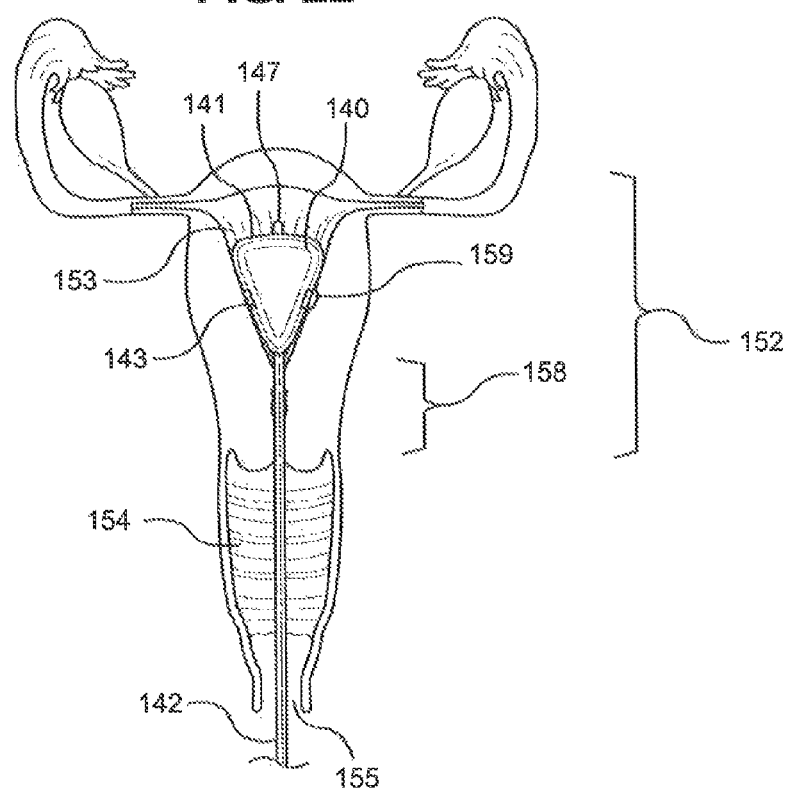
FIG. 23 is an internal antero-posterior cross-sectional view of the female reproductive anatomy showing an alternative embodiment of the Balloon Immobilization Device for Radiation Treatment of the present invention with an inflated pyriform shaped inflatable balloon within the uterus, and the flexible tube extending out of the uterus through the cervix and out the vagina.

Now referring to FIG. 23, an expanded view of the internal cross-sectional, anterior view of the female reproductive system 150 is shown with the alternate preferred embodiment of the Balloon Immobilization Device for Radiation Treatment 140 of the present invention inserted and inflated within the vaginal canal 154. The immobilization device 140 of the present invention is inserted, uninflated (as shown in FIG. 18), through the vaginal opening 155, vaginal canal 154, cervix 158 and into the corpus 153 of the uterus 152. When inserted, the inflatable oblong-shaped inflatable balloon 141 is then inflated by the first lumen 144 (not shown). The flexible tube 142 extends out of the corpus 153 of the uterus 152, through the cervix 158, vaginal canal 154, and out the vaginal opening 155.

When the pyriform-shaped inflatable balloon 141 is inflated, the corpus 153 of the uterus 152 is fixed at a constant shape and volume, and tumor 159 is fixed at a particular position. In addition, radiopaque markers 143 are used to guide health care providers to the precise position of the tumor 159 located on the inner wall of the corpus 153 of the uterus 152.

While there have been shown what are presently considered to be preferred embodiments of the present invention, it will be apparent to those skilled in the art that various changes and modifications can be made herein without departing from the scope and spirit of the invention.

We claim:

1. A balloon immobilization device for radiation treatment comprising:
    a flexible tube having a first end and a second end;
    a catheter tip formed on said second end of said flexible tube;
    an inflatable balloon comprising an expandable membrane having one or more areas of non-radiopaque material surrounded by a radiopaque material configured to confine the delivery of radiation through said one or more areas of non-radiopaque material and to shield a surrounding area from said radiation with said radiopaque material;
    wherein said inflatable balloon is attached to and encompassing a portion of said flexible tube, wherein said expandable membrane expands from a non-inflated size to a maximum inflated size; and
    one or more radiopaque markers contained within said area of non-radiopaque material configured as reference points to position said one or more areas of non-radiopaque material over a treatment area.

2. The balloon immobilization device for radiation treatment of claim 1, wherein the radiopacity of said radiopaque markers is higher than said radiopaque material.

3. The balloon immobilization device for radiation treatment of claim 2, wherein said inflatable balloon has a spherical shape.

4. The balloon immobilization device for radiation treatment of claim 2, wherein said inflatable balloon has a pyri-form shape.

5. The balloon immobilization device for radiation treatment of claim 2, wherein said inflatable balloon has an oblong shape.

6. A balloon immobilization device for radiation treatment comprising:
    a flexible tube having a first end and a second end, said flexible tube furcated into a first lumen and a second lumen;
    a catheter tip formed on said second end of said flexible tube;
    a radiopaque inflatable balloon comprising an expandable membrane attached to and encompassing a portion of said flexible tube, said expandable membrane with an interior surface and an exterior surface, said interior surface defining an interior cavity between said stretchable membrane and said flexible tube, wherein said inflatable balloon expands from a non-inflated size to a maximum inflated size and has one or more areas of non-radiopaque material configured to confine the delivery of radiation through said one or more areas of non-radiopaque material and to shield a surrounding area from said radiation with said radiopaque inflatable balloon; and
    one or more radiopaque markers attached to said areas of non-radiopaque material configured as reference points to position said areas of non-radiopaque material over a treatment area.

7. The balloon immobilization device for radiation treatment of claim 6, wherein said first end of said flexible tube is formed with a first lumen tube and a second lumen tube, said first lumen extends from a first opening in said catheter tip into said first lumen tube, and said second lumen extends from a second opening formed in said flexible tube encompassed by said inflatable balloon and exposed to the interior cavity of said inflatable balloon to said second lumen tube.

8. The balloon immobilization device for radiation treatment of claim 7, wherein the radiopacity of said radiopaque markers is higher than said radiopaque material.

9. The balloon immobilization device for radiation treatment of claim 8, wherein said radiopaque markers are positioned equidistance apart and maintain equidistance as said inflatable balloon expands between said non-inflated size and said maximum inflated size.

10. The balloon immobilization device for radiation treatment of claim 9, wherein said flexible tube is further formed with distance measurement markers.

11. The balloon immobilization device for radiation treatment of claim 6, wherein said flexible tube is further furcated to include a third lumen and said first end of said flexible tube is further formed with a third lumen tube, said third lumen extends from a third opening in said catheter tip into said third lumen tube.

12. The balloon immobilization device for radiation treatment of claim 11, wherein said inflatable balloon further comprises a plurality of radiopaque markers attached to said inflatable balloon.

13. The balloon immobilization device for radiation treatment of claim 12, wherein the radiopacity of said radiopaque markers is higher than said radiopaque material of said inflatable balloon.

14. The balloon immobilization device for radiation treatment of claim 12, wherein said radiopaque markers are positioned equidistance apart and maintain equidistance as said inflatable balloon expands between said non-inflated size and said maximum inflated size.

15. The balloon immobilization device for radiation treatment of claim 14, wherein said flexible tube is further formed with distance measurement markers.

\* \* \* \* \*

UNITED STATES PATENT AND TRADEMARK OFFICE
CERTIFICATE OF CORRECTION

| | |
|---|---|
| PATENT NO. | : 9,895,253 B2 |
| APPLICATION NO. | : 14/444857 |
| DATED | : February 20, 2018 |
| INVENTOR(S) | : Huan Giap, Fantine Giap and Bosco Giap |

It is certified that error appears in the above-identified patent and that said Letters Patent is hereby corrected as shown below:

On the Title Page

Item (56) references cited add --8,679,147 B2 3/2014 Isham--

Signed and Sealed this
Third Day of April, 2018

Andrei Iancu
*Director of the United States Patent and Trademark Office*